United States Patent [19]
Ripka

[11] Patent Number: 5,888,980
[45] Date of Patent: Mar. 30, 1999

[54] COMPOSITIONS FOR ENHANCING IMMUNE FUNCTION

[75] Inventor: James F. Ripka, Jacksonville, Fla.

[73] Assignee: Bio-Logic Research and Development Corporation, Jacksonville, Fla.

[21] Appl. No.: 475,173

[22] Filed: Jun. 7, 1995

Related U.S. Application Data

[63] Continuation of Ser. No. 269,914, Jun. 30, 1994, abandoned.
[51] Int. Cl.$^6$ .......................... A61K 31/16; A61K 31/17; A61K 31/435
[52] U.S. Cl. ................................. 514/21; 514/2; 514/11; 514/12; 514/18; 514/282
[58] Field of Search ................................. 514/2, 11, 12, 514/282, 21, 18

[56] References Cited

U.S. PATENT DOCUMENTS 3,254,088  5/1966  Lowenstein ................................. 546/45

OTHER PUBLICATIONS

Thurman et al., Chemical Abstracts, Vol. 101, abstract 21792. 1984.

Zozulya et al., Chemical Abstracts, Vol. 104, abstract 200794. 1986.

Ripka, Chemical Abstracts, Vol. 124, abstract 194312. 1996.

*Primary Examiner*—Richard L. Raymond
*Attorney, Agent, or Firm*—Synnestvedt & Lechner

[57] ABSTRACT

Compositions and methods for enhancing immune competence in a patient comprising a compound which functions to stimulate the immune system and a compound which functions to regulate neuroendocrine balance, the compositions being used to treat patients suffering from diseases associated with impaired immune functioning, including, for example, cancer and autoimmune diseases.

4 Claims, 2 Drawing Sheets

COMPOSITIONS FOR ENHANCING IMMUNE FUNCTION

This is a continuation of application Ser. No. 08/269,914 filed on Jun. 30, 1994, now abandoned.

FIELD OF THE INVENTION

This invention relates to compositions, including pharmaceutical compositions, for the treatment of various disease states and/or conditions. More particularly, the present invention relates to methods and compositions for the enhancement of immune functioning in an individual.

Drug therapy of diseases and/or conditions may be classified broadly into two general categories: (A) therapies in which the drug, acting substantially completely alone, achieves the desired effect, for example, alleviation of the disease or condition. Exemplary of this type of drug therapy is the administration to an individual of an antibiotic to inhibit the growth of or to kill foreign microorganisms. In general category (B), the drug stimulates the body's native defenses and/or healing mechanisms to combat the disease or condition. Exemplary of this type of drug therapy is the administration to an individual of a vaccine, which enhances the host immune response to invasion of a foreign pathogen.

It is contemplated that the methods and compositions of the present invention involve "(B) drug therapies."

REPORTED DEVELOPMENTS

Current treatment methods for conditions and/or diseases which involve loss or deterioration of immune competence, for example, AIDS, cancer and autoimmune diseases, has generally been unsatisfactory. In this connection, AZT (3'-azido-2',3'-dideoxythymodine) is generally considered as the most effective tool for the treatment of AIDS. However, recent studies have suggested that AZT provides substantially limited, if any, long-term benefit to persons suffering from AIDS or who are HIV-positive.

Similarly, radiation and chemotherapy, alone or in combination, are considered generally the treatment of choice for individuals who suffer from cancer. However, such treatment regimens have only minimally improved the mortality rates of patients suffering from certain kinds of cancer. Moreover, severe side effects from treatment involving radiation and chemotherapy are well-documented.

T-cells, which are white blood cells, are an integral part of the immune system. It has been reported in the literature that maturation of the T-cells requires the involvement of the thymus gland through the secretion of thymic hormones, including thymosins. Previous attempts to improve the functioning of the immune system have involved the administration to persons suffering from diseases, for example, cancer and infectious diseases, of compounds which stimulate the immune system, for example, thymosin. See *Internal Medicine World Report*, Vol. 6(8):11 (1991). However, such treatment regimens have generally met with mixed results. This lack of consistency may result from the tendency of such immune system-stimulating compounds, including thymosin, to behave as neurotransmitters which stimulate the pituitary-adrenal system. See R. Lloyd, *The Healing Brain: A Scientific Reader*, Guilford Press, New York, pp. 159–173 (1990). The stimulation of the pituitary-adrenal system may increase the level of serum corticosteroids, thereby decreasing the production of thymic hormones. This exacerbates thymic involution and impairment of immune functioning.

The present invention recognizes the interrelationship of the neurologic and endocrine systems and exploits this interrelationship to enhance immune functioning.

SUMMARY OF THE INVENTION

In accordance with the present invention, there is provided a composition for enhancing immune competence in a patient. The composition comprises a compound which functions to stimulate the immune system and a compound which functions to regulate neuroendocrine balance.

In preferred form, the compounds which function to stimulate the immune system are thymic hormones, cytokines, for example, lymphokines, and mixtures thereof. Particularly preferred among such compounds are thymosins, including thymosin α-1 and thymosin fraction 5, interleukins, interferons and mixtures thereof.

The compounds which function to regulate neuroendocrine balance, which involves the hypothalamus and the pituitary and adrenal glands, preferably include a hypothalamic factor or hormone, a neurocrine, an endocrine hormone, a material which functions to elicit or inhibit production of such compounds and mixtures thereof. Alternatively, the compounds which function to regulate neuroendocrine balance may be hypothalamic hormones or narcotic antagonists. Particularly preferred among such compounds are melanocyte-stimulating hormone inhibiting factor (MIF), α-melanocyte-stimulating hormone antagonist, melanostatin, naloxone, naltrexone and mixtures thereof.

Another aspect of the invention relates to a method for enhancing immune competence in a patient suffering from a chronic disease condition. The method involves the administration to a patient of a therapeutically-effective amount of a composition which regulates the neuro-endocrine-immune complex.

Embodiments of compositions of the present invention exhibit synergistic properties when administered to a patient suffering from a disease associated with loss or deterioration of immune function. This is evidenced, for example, by an increase in the length of survival which is greater than the length of survival if the patient is administered either of the involved compounds (but not both), with the total amount of both of the compounds being no greater than the administered amount of one of the compounds. Accordingly, the invention includes also within its scope a composition for enhancing immune competence comprising: (A) a first compound, a predetermined amount of which functions to stimulate the immune system; and (B) a second compound, a predetermined amount of which functions to regulate neuroendocrine balance; wherein the immune competence enhancing properties of an amount of said composition, which amount is no greater than the sum of each of said predetermined amounts, are greater than the combined immune competence enhancing properties of each of said compounds.

The compositions and methods of the present invention are useful in the treatment of various diseases or conditions in which enhancement of immune competence is desirable. Such diseases or conditions include those which are associated with immune disorders, for example, loss or deterioration of immune competence, including, for example, immune disorders that result from exposure of an individual to chronic stress conditions.

Exemplary diseases or conditions which may be treated with the compositions of the present invention include AIDS, cancer, chronic viral infections, autoimmune diseases and chronic disease states, generally.

It has been found that various embodiments of compositions of the present invention are particularly suitable for treating conditions or disease states which are associated with immune disorders. In this connection, compositions which comprise thymosin α-1 and MIF or thymosin α-1 and naloxone are particularly suitable for use in the treatment of individuals suffering from one or more diseases associated with loss or deterioration of immune competence.

DETAILED DESCRIPTION OF THE INVENTION

Figure 1:
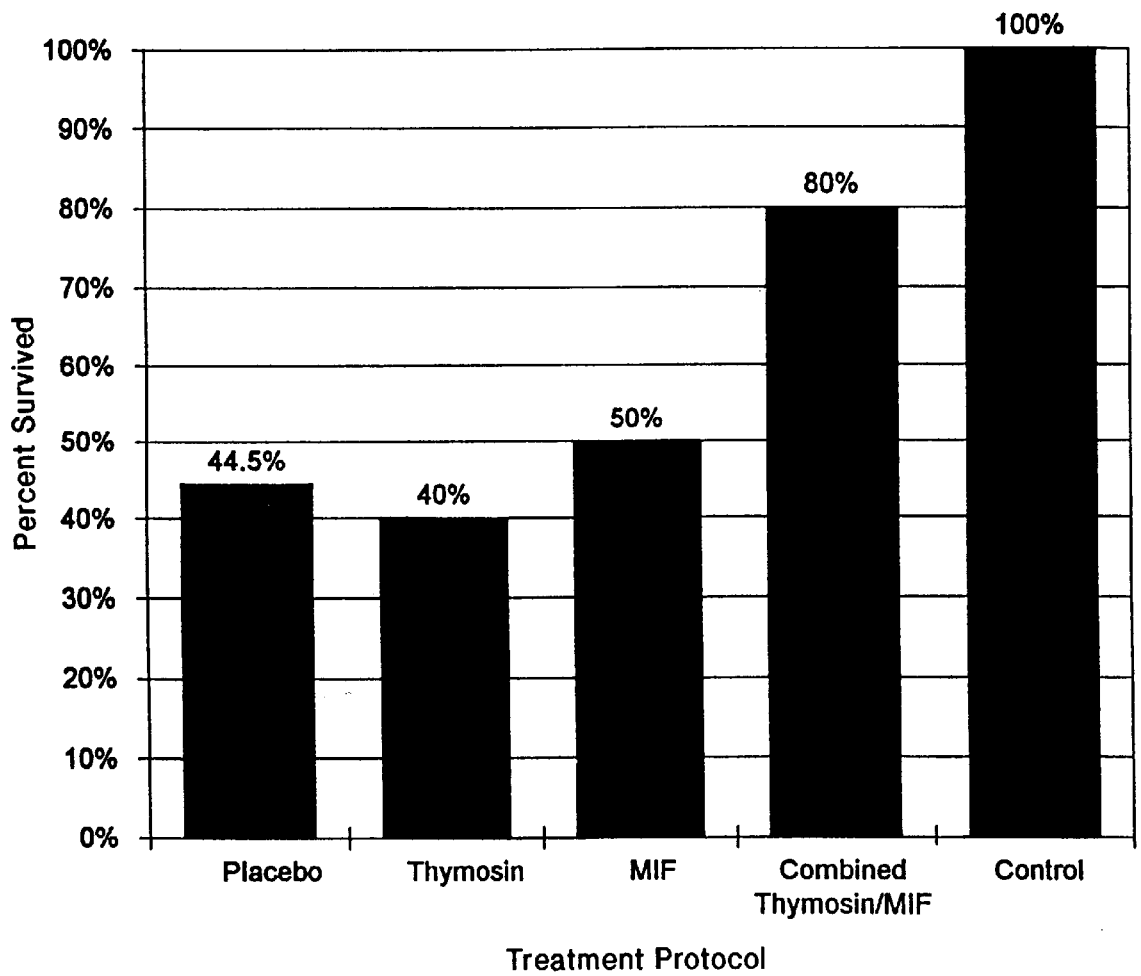
FIGS. 1 and 2 are graphical representations of studies which were conducted to evaluate the efficacy of various compositions of the present invention.

As employed above and throughout the disclosure, the following terms, unless otherwise indicated, shall be understood to have the following meanings.

"Neuroendocrine balance" refers to the synergistic relationship which is associated with the feedback loops which exist among the neurologic and endocrine systems.

"Hypothalamic-pituitary-adrenal axis" refers to the interrelationship which exists between the neurologic and endocrine systems and which involves the hypothalamus and the pituitary and adrenal glands. Unless otherwise indicated, reference to the hypothalamic-pituitary-adrenal axis includes reference to the transmitters of the neurologic and endocrine systems which influence the functioning of the axis and neuroendocrine balance, generally.

"Neuro-endocrine-immune complex" refers to the synergistic relationship which is associated with the feedback loops which exist among the neurologic, endocrine and immune systems.

"Immune competence" refers to the ability of the immune system to protect against pathogens or infectious agents.

"Stimulation of the immune system" means activation of aspects of the immune system to protect against pathogens or infectious agents.

"Immune surveillance dysfunction" refers to an immune system which is functioning improperly and which is unable to recognize and/or destroy pathogens, infectious agents and/or abnormal cells, the latter of which frequently arise within the body, for example, in the form of cancer, such as malignant melanomas and/or which identifies normal cells improperly as abnormal cells and attacks the normal cells, for example, in autoimmune diseases.

"Immunoregulatory function" refers to the ability of a compound or material to stimulate the immune system.

"Autonomic arousal" refers to the arousal of the autonomic system.

"Patient", as used herein, refers to animals, including mammals, such as humans.

The present invention provides compositions for enhancing immune competence in a patient. The compositions comprise a compound which functions to stimulate the immune system and a compound which functions to regulate neuroendocrine balance.

Compounds which function to stimulate the immune system include compounds which are capable of activating aspects of the immune system to protect against pathogens or infectious agents. However, as noted in the "Reported Developments" hereinbefore, the administration of such compounds frequently fails to provide enhanced immune functioning. By virtue of the methods and compositions of the present invention, enhancement of immune competence is achieved by administering compositions which comprise a compound which stimulates the immune system in conjunction with a compound which functions to regulate neuroendocrine balance.

Compounds which function to stimulate the immune system have been reported in the literature and include, for example, thymic hormones, cytokines and mixtures thereof. Preferred among the thymic hormones are thymosin, thymosin α-1 and thymosin fraction 5, with thymosin α-1 being particularly preferred.

The preferred compounds among the cytokines are lymphokines. Examples of suitable lymphokines are the interleukins, including interleukin 1, 2 and 3, and the interferons, including α-, β- and γ-interferon. Preferred among the lymphokines are the interleukins, with interleukins 1 and 2 being particularly preferred.

As noted above, the present compositions comprise also a compound which functions to regulate neuroendocrine balance. These compounds are capable of regulating the synergistic relationship which is associated with the feedback loops that exist among the neurologic and endocrine systems.

In various of the embodiments of the present invention, neuroendocrine balance involves the hypothalamic-pituitary-adrenal axis. The term "hypothalamic-pituitary-adrenal axis" refers to the interrelationship which exists between the neurologic and endocrine systems and which involves the hypothalamus and the pituitary and adrenal glands. It is contemplated that the hypothalamic-pituitary-adrenal axis includes also the transmitters of the neurologic and endocrine systems which influence the functioning of the axis and neuroendocrine balance, generally.

As with the compounds which function to stimulate the immune system, compounds which function to regulate neuroendocrine balance have been reported in the literature. Examples of compounds which function to regulate neuroendocrine balance and which may be used in the methods and compositions include narcotic antagonists. Preferred narcotic antagonists include naloxone, naltrexone and mixtures thereof.

Compounds which function to regulate neuroendocrine balance include also hypothalamic factors or hormones, pituitary factors or hormones, neurocrines, endocrine hormones, neuropeptides, materials which function to elicit or inhibit the production of the aforesaid compounds and mixtures thereof. Preferred among such compounds are melanocyte-stimulating hormone inhibiting factor, including MIF and MIF-1, α-melanocyte-stimulating hormone (MSH) antagonist, melanostatin, somatostatin, somatotropin, thyrotropin, dopamine, α and β endorphin, growth hormone, α- and β-adrenergic blockers, prolactin and mixtures thereof. Preferred among the aforesaid compounds are melanocyte-stimulating hormone inhibiting factor and α-melanocyte-stimulating hormone antagonist, with melanocyte-stimulating hormone inhibiting factor being particularly preferred.

A preferred melanocyte-stimulating hormone inhibiting factor is the hypothalamic tripeptide Pro-Leu-Gly amide.

Selection of compounds which function to stimulate the immune system and compounds which function to regulate neuroendocrine balance, examples of which are described hereinbefore, depends upon various factors. For example, selection may be based upon the particular disease or condition being treated and the physiological characteristics of the particular patient under treatment. In this connection, cancerous conditions may be treated with compositions that comprise compounds which involve the immune suppressor arm of the neuroendocrine system, for example, to block the production of α-melanocyte-stimulating hormone through administration of melanocyte-stimulating hormone inhibiting factor, and a compound which activates the natural killer (NK) cytotoxic cells through administration of interleukin 1 or 2. In T-cell deficiency conditions, administration of thymic hormone and interleukin 2 will stimulate the immune system. However, it is important also to simultaneously control the feedback loop involving the thymic hormone and the endocrine system via administration of a narcotic antagonist, such as naloxone or naltrexone.

In accordance with the present invention, the compositions preferably comprise the compound which functions to stimulate the immune system and the compound which functions to regulate neuroendocrine balance in amounts which result in therapeutic effect, that is, to obtain at least partial alleviation of, or improvement in, the condition or disease. (For convenience only, and not by way of limitation, the compound which functions to stimulate the immune system is referred to hereinafter as "compound (IS)" and the compound which functions to regulate neuroendocrine balance is referred to hereinafter as "compound (NB)".) The amounts of each of compound (IS) and compound (NB) in a given composition depend upon various factors, including, for example, the specific compounds selected, the disease or condition being treated, and the physiological characteristics of the patient.

In various preferred embodiments of the invention, the compositions comprise at least about 20 wt. % of compound (IS) and at least about 30 wt. % of compound (NB). In preferred form, the compositions comprise about 20 to about 50 wt. % of compound (IS) and about 30 to about 70 wt. % of compound (NB). More preferably, the compositions comprise about 30 to about 40 wt. % of compound (IS) and about 60 to about 70 wt. % of compound (NB).

The ratio of compound (IS) to compound (NB) may vary and depends, for example, upon the specific compound selected, the disease or condition being treated and the physiological characteristics of the patient. Preferably, the ratio of the compounds is selected to achieve a therapeutic effect as described hereinbefore.

In various preferred embodiments, the ratio of compound (IS) to compound (NB) is about 1:1 to about 1:4, with about 1:1.5 to about 1:3.5 being preferred.

The compositions of the present invention can be administered to a mammalian host in a variety of forms adapted to the chosen route of administration, i.e., orally, parenterally or intraperitoneally. Parenteral administration in this respect includes administration by the following routes: intravenous, intramuscular, subcutaneous, intraocular, intrasynovial, transepithelial including transdermal, ophthalmic, sublingual and buccal; topically including ophthalmic, dermal, ocular, rectal and nasal inhalation via insufflation and aerosol and rectal systemic.

The compositions may also be orally administered, for example, with an inert diluent or with an assimilable edible carrier, or it may be enclosed in hard or soft shell gelatin capsules, or it may be compressed into tablets, or it may be incorporated directly with the food of the diet. For oral therapeutic administration, the compositions may be incorporated with excipient and used in the form of ingestible tablets, buccal tablets, troches, capsules, elixirs, suspensions, syrups, wafers, and the like.

The tablets, troches, pills, capsules and the like may also contain the following: a binder, such as gum tragacanth, acacia, corn starch or gelatin; excipients, such as dicalcium phosphate; a disintegrating agent, such as corn starch, potato starch, alginic acid and the like; a lubricant, such as magnesium stearate. A sweetening agent, such as sucrose, lactose or saccharin, or a flavoring agent, such as peppermint, oil of wintergreen, or cherry flavoring may be added. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavoring, such as cherry or orange flavor. Of course, any material used in preparing any dosage unit form should be pharmaceutically pure and substantially non-toxic in the amounts employed. In addition, the compositions may be incorporated into sustained-release preparations and formulations.

Solutions of the compositions which comprise active compounds as the free acid or base or pharmacologically acceptable salt can be prepared in water suitably mixed with a surfactant, such as hydroxypropylcellulose. Dispersions can also be prepared in glycerol, liquid polyethylene glycols, and mixtures thereof, and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that it is easy to draw into, and discharge from, a syringe. It may be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by use of agents delaying absorption, for example, aluminum monostearate and gelatin.

Sterile injectable solutions are prepared by incorporating the compositions in the required amounts in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum drying and the freeze drying technique which yield a powder of the active ingredient, plus any additional desired ingredient from previously sterile-filtered solutions thereof.

The therapeutic compositions of this invention may be administered to a mammal alone or in combination with pharmaceutically acceptable carriers, as noted above, the proportion of which is determined by the solubility and chemical nature of the selected compounds, chosen route of administration and standard pharmaceutical practice.

The compositions of the present invention are particularly suitable for the treatment of diseases which result from immune surveillance dysfunction. The term "immune surveillance dysfunction" refers to an immune system which is functioning improperly and which is unable to recognize and/or destroy pathogens, infectious agents and/or abnormal cells, or which identifies normal cells improperly as abnormal cells and attacks the normal cells, for example, in autoimmune diseases. The present compositions are particularly suitable for the treatment of diseases which are associated with immune surveillance dysfunction in that they involve compounds which stimulate the immune system and regulate neuroendocrine functions. It is contemplated that in various preferred embodiments, the compositions enhance immune competence by regulating the neuro-endocrine-immune complex. The term "neuro-endocrine-immune complex" refers to the synergistic relationship which is associated with the feedback loops which exist among the neurologic, endocrine and immune systems. Also in various preferred embodiments, the present compositions regulate autonomic arousal which refers to the ability of the compositions to regulate arousal of the autonomic system.

Diseases which may be treated with the present compositions include pathologies or conditions which are associated with immune systems that have been compromised, resulting in loss or deterioration of immune competence. The loss or deterioration of immune competence is associated, for example, with immune systems which have been compromised from exposure of a patient to chronic stress conditions. It has been reported that exposure to chronic stress conditions results in a dysfunction of serum thymic hormone levels or thymic involution.

Exemplary conditions or diseases which may be treated with the compositions of the present invention include AIDS, cancer, chronic viral infections, autoimmune diseases and chronic disease states. Although it is contemplated that the present compositions may be used to treat a variety of cancers, they are particularly suitable for the treatment of malignant melanomas. Compositions for the treatment of melanomas preferably comprise a compound having immunoregulatory function and a compound which regulates the release of melanocyte-stimulating hormone.

The present compositions may enhance immune competence also by influencing the genetic recombination of lymphocytes.

The dosage of the present therapeutic compositions which will be most suitable for prophylaxis or treatment will vary with the form of administration, the particular compounds chosen and the physiological characteristics of the particular patient under treatment. Generally, small dosages will be used initially and if necessary, will be increased by small increments until the optimum effect under the circumstances is reached. The therapeutic human dosage, based on physiological studies using rats, will generally be from about 0.02 to about 20 mg/m$^2$, based on the body surface area of the individual, of the present compositions. It is contemplated that this dosage range involves about 0.01 to about 10 mg/m$^2$, based on the body surface area, of one or more compounds which function to stimulate the immune system, and about 0.01 to about 10 mg/m$^2$, based on the body surface area, of one or more compounds which function to regulate neuroendocrine balance.

In the alternative, the therapeutic human dosage, based also on physiological studies using rats, will generally be from about 0.01 mg to about 100 mg/kg of body weight per day or from about 0.4 mg to about 10 g or and higher although it may be administered in several different dosage units from once to several times a day. Oral administration requires higher dosages.

Such compositions and preparations should contain the active compounds in amounts to obtain the desired therapeutic effect. The percentage of the compounds in the present compositions and preparations may, of course, be varied. The amounts of active compounds in such therapeutically useful compositions is such that a suitable dosage will be obtained. Preferred compositions or preparations according to the present invention are prepared so that an oral dosage unit form contains between about 5 and 100 mg of active compounds.

It is believed that the present invention will be practiced most widely by administering a composition which includes a compound which stimulates the immune system and a compound which regulates neuroendocrine balance. However, it should be understood that the present invention can be practiced also by administering each of the involved compounds separately.

EXAMPLES

Embodiments of the present invention are described in the following examples which include a description of pharmacological test procedures believed to correlate to therapeutic activity in humans and other animals. The test procedures involved a comparison of the efficacy for treating immune disorders of mixtures of compounds according to the present invention to the efficacy of compounds of the prior art.

Example 1

This example includes a description of a study which involved 60 albino mice, each of which was about 7 months old and weighed 30 to 45 grams. The mice had no known predisposition to any disease or dysfunction.

The mice were divided randomly into two groups: (A) non-stress control group (10 mice); and (B) experimental group to be subjected to stress (50 mice).

The group A mice were placed in a 10-gallon glass tank which included a bedding of cedar shavings and a play wheel. Food and water were available to the mice at all times. The tank was situated in a controlled environment in which the temperature was maintained at about room temperature (22° C.).

The group B mice were divided randomly into two subgroups ($B_a$ and $B_b$). The $B_a$ and $B_b$ groups were each placed into separate 10-gallon glass tanks which were situated in a refrigeration unit. The average temperature in the refrigeration unit was maintained at about 0.5° C. Each tank included a bedding of cedar shavings and a play wheel; food and water were available to the mice at all times.

After 109 days in the refrigeration unit, 11 mice in the $B_a$ and $B_b$ groups died. The surviving 39 mice were combined and divided randomly into four groups: (1) $B_1$ (10 mice); (2) $B_2$ (10 mice); (3) $B_3$ (10 mice); and (4) $B_4$ (9 mice).

The next phase of the study involved exposing the $B_1$, $B_2$, $B_3$ and $B_4$ mice to about a freezing temperature for 34 weeks while administering a selected treatment protocol. This involved placing the $B_1$, $B_2$, $B_3$ and $B_4$ mice into separate 5-gallon glass tanks that were situated in the refrigeration unit described above. (The temperature in the refrigeration unit was again maintained at about 0.5° C.) Each of the 5-gallon tanks included a bedding of cedar shavings and a play wheel; food and water were available to the mice at all times. To simulate daylight, the glass tanks were exposed to lighting each day from about 7:00 a.m. to about 9:00 p.m.

The $B_1$, $B_2$, $B_3$ and $B_4$ mice were subjected to treatment protocols which involved the administration of a mixture of compounds according to the invention, comparative compounds, including prior art compounds and placebo (sterile water), as set forth in the following table.

TABLE I

| Group | Treatment Protocol Compound(s) Amount |
|---|---|
| $B_1$ | C-1, thymosin α-1 (25 μg) |
| $B_2$ | C-2, MIF (35 μg) |
| $B_3$ | I-1, thymosin α-1 (25 μg) and MIF (35 μg) |
| $B_4$ | C-3, sterile water (0.02 ml) |

During the first 24 days of the study, the above compounds were administered subcutaneously each day. Thereafter, and for the duration of the 34-week study, the compounds were administered subcutaneously every other day.

The efficacy of each of the treatment protocols was measured by the length of survival in days for each mouse and the number of surviving mice in each group at the end of the study. This is depicted in FIG. 1 which shows graphically the number of mice surviving in groups A, $B_1$, $B_2$, $B_3$ and $B_4$. All ten mice in the non-stress control group (A) survived the study. Four mice in the group which received thymosin only ($B_1$) survived and five mice in the group which received MIF only ($B_2$) survived. Eight mice in the group which received mixtures of compounds according to the invention ($B_3$) survived. (One mouse in the $B_3$ group died accidentally during subcutaneous administration.) Four mice in the group which received placebo ($B_4$) survived.

The mean length of survival for the non-stress control group (A) was 238 days (34 weeks). The thymosin (C-1) group ($B_1$) and the MIF (C-2) group ($B_2$) had mean lengths of survival of 197.8 and 206.8 days, respectively. The mean length of survival for the combined thymosin/MIF (I-1) group ($B_3$) was 222.9 days, and that of the placebo (C-3) group ($B_4$) was 194.4 days.

Data for individual and group survival of the mice involved in the study is tabulated in Table II.

Inspection of Table II above reveals that the length of survival of the group of mice which received the mixtures of compounds (I-1) according to the invention ($B_3$) and the non-stress control group (A) was substantially similar. However, a significant difference in length of survival was observed between the mice receiving compounds of the prior art, namely, thymosin (C-1) or MIF (C-2) only ($B_1$ and $B_2$), and the non-stress control group (A). In particular, the mice in the $B_1$ and $B_2$ groups had significantly shorter lengths of survival than the mice in the (A) group. In addition, the mice which received thymosin (C-1) or MIF (C-2) only ($B_1$ and $B_2$) and the mice which received placebo (C-3; $B_4$) had a significantly shorter length of survival as compared to the mice which received thymosin and MIF combined (I-1; $B_3$).

For adjunct data, autopsies were performed on the mice which died. The autopsies revealed the occurrence of significant thymic involution and adrenal hypertrophy. Other stress-induced pathologies, for example, ulcerated stomachs, enlarged hearts and fibrous tumors were observed also in various of the mice which were autopsied. The mice which were autopsied exhibited an average loss of body weight of 39%.

Several mice from the non-stress control group (A) were sacrificed after the end of the study. These mice had intact thymus glands and normal adrenal glands. Similarly, four mice from the group receiving the mixtures of compounds (I-1) according to the invention ($B_3$) were sacrificed. All of the $B_3$ mice had intact thymus glands and normal adrenal glands and were otherwise devoid of pathology.

Example 2

The study described in this example involved 30 albino mice, each of which was about three months old and weighed 30 to 40 grams. The mice, which had no known predisposition to any disease or dysfunction, were subjected to about a freezing temperature for 20 weeks while being treated with a selected compound or mixtures of compounds.

The mice were first divided randomly into six groups (Groups (1) to (6)), each of which comprised five mice. The six groups were each placed into separate five-gallon glass tanks which were situated in a refrigeration unit. The average temperature in the refrigeration unit was maintained at about −1.0° C. Each tank included a bedding of cedar shavings and a play wheel; food and water were available to the mice at all times. To simulate daylight, the glass tanks were exposed to lighting from about 7:00 a.m. to about 9:00 p.m.

Each of groups (1) to (6) was subjected to selected treatment protocols which involved the administration to the mice of mixtures of compounds according to the invention, and comparative compounds, including prior art compounds and placebo (sterile water), as set forth in Table III.

TABLE II

| Group | No. of Mice in Group | Length of Survival of Mice (days) | | | | | | | | | | Mean |
|---|---|---|---|---|---|---|---|---|---|---|---|---|
| A | 10 | 238 | 238 | 238 | 238 | 238 | 238 | 238 | 238 | 238 | 238 | 238 |
| $B_1$ | 10 | 128 | 157 | 165 | 189 | 189 | 198 | 238 | 238 | 238 | 238 | 197.8 |
| $B_2$ | 10 | 156 | 162 | 184 | 188 | 188 | 238 | 238 | 238 | 238 | 238 | 206.8 |
| $B_3$ | 10 | 110 | 215 | 238 | 238 | 238 | 238 | 238 | 238 | 238 | 238 | 222.9 |
| $B_4$ | 9 | 144 | 147 | 148 | 171 | 188 | 238 | 238 | 238 | 238 | — | 194.4 |

TABLE III

| Group | Treatment Protocoi Comnound(s), Amount |
|---|---|
| 1 | C-4, thymosin α-1 (10 μg) |
| 2 | C-5, MIF (25 μg) |

TABLE III-continued

| Group | Treatment Protocol Compound(s), Amount |
|---|---|
| 3 | C-6, naloxone (25 μg) |
| 4 | I-2, MIF (25 μg) and thymosin α-1. (10 μg) |
| 5 | I-3, naloxone (25 μg) and thymosin α-1 (10 μg) |
| 6 | C-7, sterile water (0.01 ml) |

During the first three weeks of the study, the above compounds were administered subcutaneously each day. Thereafter, and for the duration of the 20-week study, the compounds were administered subcutaneously every other day.

Figure 2:
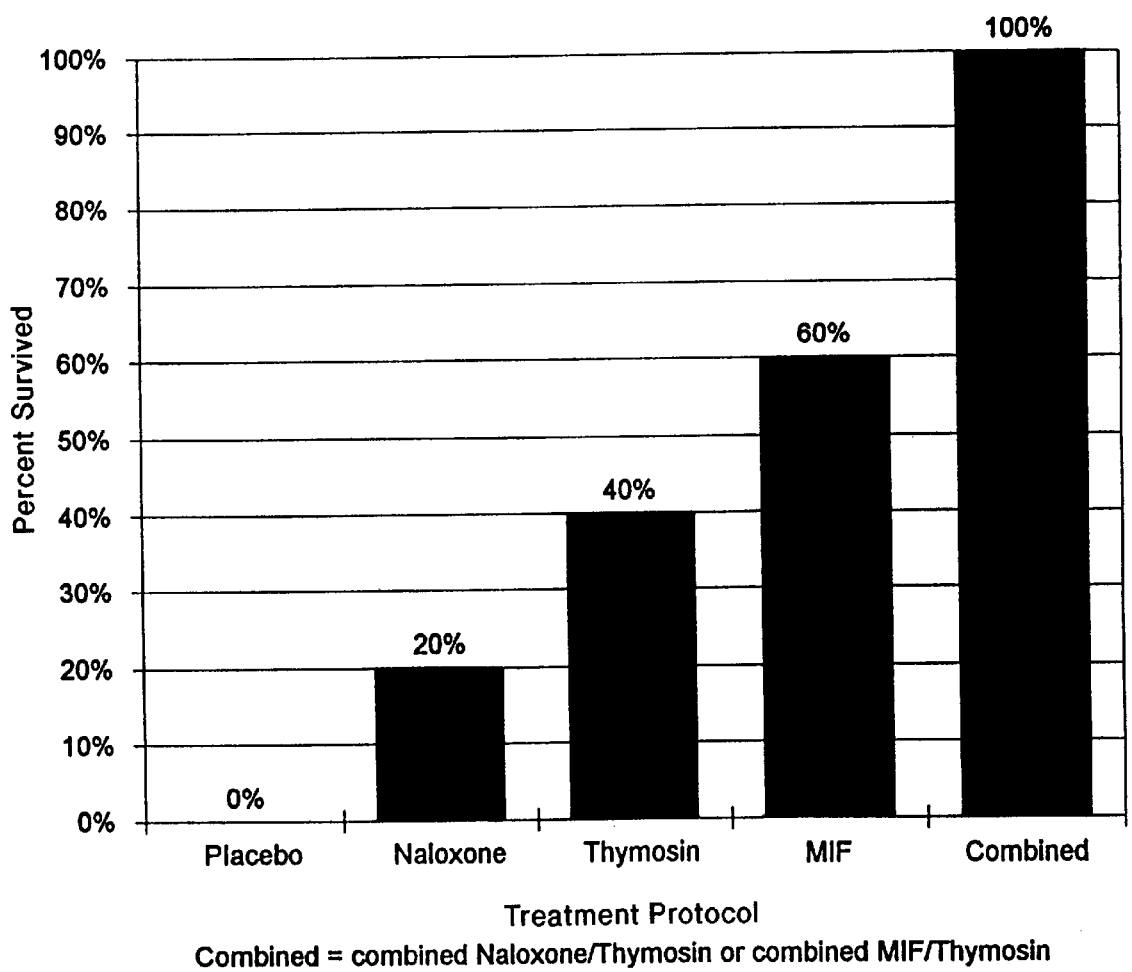

The efficacy of each of the treatment protocols was measured by the length of survival in days for each mouse and the number of surviving mice in each group at the end of the study. This is depicted in FIG. 2 which shows graphically the number of mice surviving in groups (1) to (6). All of the mice in the groups which received both thymosin α-1 and MIF (I-2; group 4) and naloxone and thymosin α-1 (I-3; group 5) survived. Two mice survived in the group which received thymosin α-1 only (C-4; group 1); three mice survived in the group which received MIF only (C-5; group 2); and only one mouse survived in the group which received naloxone only (C-6; group 3). All of the mice in the group which received placebo (C-7; group 6) died.

The mean length of survival for the group which received thymosin only (C-4; group 1) was 85.8 days and for the group which received MIF only (C-5; group 2) was 89.4 days. The group which received naloxone only (C-6; group 3) had a mean length of survival of 99.6 days. The mean length of survival for the groups receiving mixtures of thymosin and MIF (I-4; group 4), as well as for the group receiving mixtures of naloxone and thymosin (I-3; group 5), was 140 days. The mean length of survival for the control group (C-7; group 6) was 97 days.

There was a significant difference in the mean length of survival for each of the combined treatment conditions (I-2 and I-3; groups 4 and 5) and the control group (C-7; group 6). The mean lengths of survival for each of the groups receiving single compounds (C-4 to C-6; groups 1 to 3) and the control group (C-7; group 6) were substantially similar.

Autopsies were performed for adjunct data which revealed significant thymic involution in the mice of the control group (C-7; group 6) compared to normal mice generally.

Autopsies revealed also evidence of stress-related pathology in both the control (C-7; group 6) and single treatment protocol groups (C-4 to C-6; groups 1 to 3). The mice from the combined treatment groups (I-2 and I-3; groups 4 and 5) were sacrificed and post-mortem dissections showed normal thymus glands and no observable pathologies.

Example 3

This example includes a description of a proposed treatment protocol for asymptomatic, HIV positive subjects. The treatment, which is designed to improve immunological functioning, is based on the concept that reciprocal interactions between the neuroendocrine system and the immune system influence immune competence.

The subjects in the experimental treatment model consist of 12 asymptomatic HIV-positive males, ranging in age from 21 to 55, and with CD4 counts of 400 to 500. The subjects have no medical condition requiring prescription drugs. For the duration of the treatment study, the subjects abstain from the use of alcohol and drugs, including over-the-counter medications and health supplements.

To establish each subject's baseline, total CD4 and CD8 counts and CD4/CD8 ratios are taken three times, each at 30-day intervals. Treatment is started on the day that the third baseline counts are completed. For the next 90 days, the subjects receive subcutaneous injections of thymosin α-1 (1 mg/m$^2$ body surface area) three times per week. On a daily basis, the subjects take orally clonidine hydrochloride (0.01 mg/kg b.i.d.), and arginine (0.12 gm/kg b.i.d.). Total CD4s, CD8s, and CD4/CD8 ratios are taken every 30 days until completion of the 90-day treatment regimen. At the end of the 90-day treatment period, the subjects are weaned off clonidine hydrochloride. Post-treatment CD4 and CD8 counts, as well as CD4/CD8 ratios are taken every 30 days for another 90 days. An analysis of variance is done to compare the pre-treatment, treatment, and post-treatment data on total CD4s, CD8s, and CD4/CD8 ratios. A p value of <0.05 is considered significant.

Example 4

This example includes a treatment model which addresses the interactions of the neurologic-endocrine-immune complex in malignant melanomas. The model is derived from research observations on melanomas. Treatment is based on the supposition that neuroendocrine suppression of MSH would enhance the effectiveness of immune modulation. This is accomplished by the simultaneous administration of a polypeptide, for example, melanocyte stimulating hormone inhibiting factor (melanostatin), which inhibits the release or production of MSH, and compounds with immunoregulatory effects, such as thymic hormones, and cytokines, for example, lymphokines.

I claim:

1. A composition for enhancing immune competence in a patient comprising thymosin as a compound which functions to stimulate the immune system and naloxone as a compound which functions to regulate neuroendocrine balance.

2. A composition for enhancing immune competence in a patient comprising thymosin α-1 as a compound which functions to stimulate the immune system and melanocyte-stimulating hormone inhibiting factor (MIF) as a compound which functions to regulate neuroendocrine balance.

3. A method for enhancing immune competence in a patient in need of such treatment comprising administering to said patient a therapeutically-effective amount of a composition according to claim 1.

4. A method for enhancing immune competence in a patient in need of such treatment comprising administering to said patient a therapeutically-effective amount of a composition according to claim 2.

* * * * *